US00PP36727P2

(12) United States Plant Patent
Kordes

(10) Patent No.: US PP36,727 P2
(45) Date of Patent: Jun. 10, 2025

(54) FLORIBUNDA ROSE PLANT NAMED 'KORneukap'

(50) Latin Name: *Rosa hybrida*
Varietal Denomination: KORneukap

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 19/042,162

(22) Filed: Jan. 31, 2025

(51) Int. Cl.
*A01H 5/02* (2018.01)
*A01H 6/74* (2018.01)

(52) U.S. Cl.
USPC ..... Plt./146
CPC ..... *A01H 6/749* (2018.05)

(58) Field of Classification Search
USPC ..... Plt./146
CPC ..... A01H 6/749; A01H 5/02
See application file for complete search history.

(56) References Cited

U.S. PATENT DOCUMENTS

PP29,399 P3 6/2018 Kordes
PP31,256 P2 12/2019 Kordes

OTHER PUBLICATIONS

Ludwig's Roses 2024 Catalogue (https://www.ludwigsroses.co.za/2024-catalogue/) (Mar. 2024), front cover, pp. 2, 85, 110, back cover.

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of floribunda rose plant, referred to by its cultivar name, 'KORneukap', is described. The new variety forms in abundance on a substantially continuous basis, orange-colored blossoms. The growth habit is very bushy and upright. Glossy, dark green ornamental foliage is formed. Additionally, the new variety is particularly well suited for growing as distinctive ornamentation in the landscape.

1 Drawing Sheet

Latin name of genus and species of plant claimed: *Rosa hybrida.*

Variety denomination: 'KORneukap'.

STATEMENT REGARDING PRIOR DISCLOSURES BY THE INVENTOR

The first sale or offer for sale of the new variety was March 2024, in the Ludwig's Roses 2024 Catalog. The first sale or offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of floribunda rose plant of the present invention was created by controlled breeding during May 2012, in Offenseth-Sparrieshoop, Germany by artificial pollination wherein two parents were crossed which previously had been studied in the hope that they would contribute the desired characteristics. The female parent (i.e., the seed parent) of the new variety was an unnamed breeder seedling (not patented). The male parent (i.e., the pollen parent) of the new variety was the 'KORrosobi' variety (U.S. Plant Pat. No. 31,256).

The parentage of the new variety can be summarized as follows:

unnamed breeder seedling x 'KORrosobi'

The seeds resulting from the above pollination were sown and small plants were obtained which were physically and biologically different from each other. Selective study resulted in the identification of a single plant of the new variety.

The new variety has been found to undergo asexual propagation in Wasco, California and Cochranville, Pennsylvania by a number of routes such as vegetative cuttings. Asexual propagation techniques in Wasco, California and Cochranville, Pennsylvania, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of floribunda rose plant of the present invention possesses the following combination of characteristics:

(a) forming orange-colored blossoms, (b) exhibiting a very bushy and upright growth habit, and (c) providing ornamental glossy, dark green foliage.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the new variety displays a higher petal count compared to the unnamed breeder seedling (i.e., the seed parent). Additionally, the new variety displays a lower petal count, exhibits a more upright and vigorous growth habit, and forms a rounder flower shape compared to the 'KORrosobi' variety (i.e., the pollen parent). Moreover, the new variety can be readily distinguished from non-parental related similar varieties. For example, the new variety exhibits a taller growth habit, forms a larger flower size, and displays a lower petal count compared to the 'KORfloci109' variety (U.S. Plant Pat. No. 29,399).

The new variety has been named the 'KORneukap' variety.

BRIEF DESCRIPTION OF THE PHOTOGRAPHS

The accompanying photograph shows, as nearly true as it is reasonably possible to make the same in a color illustration of this character, a typical specimen of the new variety and blossoms of the new variety. The illustrated rose plant of the new variety was approximately two years of age and was grown outdoors in a field in Cochranville, Pennsylvania in June 2023.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a three-year-old specimen of the new variety, observed during August, while growing on its own roots in a field in Cochranville, Pennsylvania.

Botanical classification: *Rosa hybrida* cultivar 'KORneukap'.

Commercial classification: Floribunda Rose.

Plant:

*Habit*.—Bushy and upright.

*Height*.—Approximately 91.0 cm on average from the top of the soil plane when growing in the ground.

*Width*.—Approximately 91.0 cm on average.

Branches:

*Stem color*.—Old wood: Yellow-Green Group 144A. — young stems: Greyed-Purple Group 185A.

*Length*.—Main stems: approximately 91.0 cm on average. — secondary stems: approximately 50.0 cm on average.

*Diameter*.—Main stems: approximately 2.0 cm on average. — secondary stems: approximately 6.0 mm on average.

*Texture*.—Smooth.

*Prickles*.—Amount: few to no prickles on top half of plant; 3 to 4 prickles per internode on main stems of lower half of plant. — young prickles: length is approximately 2.0 mm on average; width is approximately 2.0 mm on average at point of attachment; and color is Greyed-Purple Group 187C. — old prickles: length is approximately 7.0 mm on average; width is approximately 9.0 mm on average at point of attachment; and color is Greyed-Orange Group 177B.

Leaflets:

*Number*.—3, 5, and 7.

*Shape*.—Ovate; apex is acute to acuminate; and base is cuneate.

*Arrangement*.—Odd-pinnate.

*Margin*.—Serrate.

*Undulation*.—Moderate.

*Glossiness of upper side*.—Glossy.

*Texture*.—Upper surface: smooth. — under surface: smooth.

*Venation pattern*.—Reticulate.

Size.—Terminal leaflet: length is approximately 7.1 cm on average; width is approximately 4.0 cm on average. — lower leaflets: length is typically 4.0 cm to 5.0 cm; width is typically 2.5 cm to 3.0 cm. — 5-Leaflet leaf. length is approximately 13.0 cm on average; width is approximately 9.5 cm on average.

Foliage:

*Young foliage*.—Upper surface color: Green Group 137B with Greyed-Purple Group 185A around the edges, with indistinguishable venation. — under surface color: Green Group 138A and Greyed-Purple Group 187C with venation of Greyed-Purple Group 187C.

*Old foliage*.—Upper surface color: Green Group 139A with indistinguishable venation. — under surface color: Green Group 138A with venation of Yellow-Green Group 146C.

*Petiole*.—Texture: upper surface is hispidulous; under surface is minutely thorny. — length: approximately 2.6 cm on average. — width: approximately 1.0 mm on average. — upper surface color: Greyed-Purple Group 183A. — under surface color: Yellow-Green Group 144A.

*Rachis*.—Length: approximately 2.5 cm on average. — width: approximately 1.0 mm on average. — upper surface color: Greyed-Purple Group 185A. — under surface color: Yellow-Green Group 144A.

*Stipules*.—Length: approximately 1.6 cm on average. — width: approximately 3.0 mm on average. — margin: entire to erose. — upper surface color: Yellow-Green Group 144A. — lower surface color: Yellow-Green Group 144A.

Inflorescence:

*Number of flowers*.—About 20 to 25 blooms on average on a plant at once.

*Number of blossoms per stem or in a cluster*.—Typically 1 bloom per stem on average.

*Peduncle*.—Color: Red-Purple Group 59A and Green Group 143C. — diameter: approximately 1.0 mm on average. — length: approximately 5.5 cm on average. — surface texture: hispidulous.

*Sepals*.—Number: 5. — upper surface color and texture: Green Group 138A and Greyed-Purple Group 184A, hispidulous. — under surface color and texture: Greyed-Orange Group 176B, puberulent. — size: length is approximately 3.6 cm on average; width is approximately 8.0 mm on average. — margin: entire with extensions on most sepals measuring approximately 6.0 mm in length and 1.0 mm in width on average. — undulation: minimal. — shape: lanceolate. — apex: acute to aristate. — base: truncate as it joins the receptacle.

*Buds*.—Shape: ovoid. — size: length is approximately 2.3 cm on average; width is approximately 8.0 mm on average. — color (when opening): largely Orange-Red Group N30A, with some Yellow-Orange Group 21A at the base and around the petal margin.

*Flower*.—Form: double, cuplike. — profile: concave as it opens, and then outer petals are convex as the bloom ages and opens further. — diameter: approximately 9.0 cm on average. — height: approximately 5.0 cm on average. — duration: on the plant approximately 10 to 12 days. — petal color when first and fully opened: upper surface of inner petals is Red Group 37B, fading downwards to Yellow-Orange Group 14A at the base with no distinct basal spot, upper surface of outer petals is Red Group 39A and Red Group 39C with Yellow Group 13A at the base with no distinct basal spot; under surface of inner petals is Red Group 37B, fading downwards to Yellow Group 9B at the base with no distinct basal spot, under surface of outer petals is Red Group 37A at apex and Yellow Group 7A at the base with no distinct basal spot. — petal color at end of bloom: upper surface is Red-Purple Group 61C at apex fading to Red-Purple Group 62C mid-petal and Yellow Group 9A at the base with no distinct basal spot; under surface is Red-Purple Group 61C around the margin with mainly Red-Purple Group 63D and Yellow Group 9C at the base with no distinct basal spot. — petals reflex: one by one: yes.

*Fragrance*.—Strong sweet scent.

*Petal*.—Number: 25 to 30 on average. — drop: good. — length: typically 4.0 cm to 4.5 cm. — width: typically 3.5 cm to 4.8 cm. — overall shape: broadly obovate. — margin: entire with moderate undulation. — apex shape: rounded to slightly cuspidate. — base shape: cuneate. — texture: upper surface is smooth; under surface is smooth.

*Petaloids*.—Number: approximately 4 on average. — length: approximately 3.6 cm on average. — width: approximately 1.5 cm on average. — color: upper and under surfaces are Orange-Red Group 31B with Yellow Group 9A at the base. — texture: upper surface is smooth; under surface is smooth. — margin: entire. — shape: obovate. — apex: rounded to slightly cuspidate. — base: cuneate.

*Stamen*.—Number: approximately 161. — anthers: number is approximately 161; color is Yellow-Orange Group 17A; length is approximately 2.0 mm on average; and shape is oval. — filaments: length is approximately 8.0 mm on average and color is Yellow-Orange Group 17A.

*Pistils*.—Arrangement: separate and free. — number: approximately 80. — style: length is approximately 8.0 mm on average and color is Red Group 39A. — stigma: diameter is approximately 1.0 mm on average; shape is fan shaped; color is Yellow Group 8B.

*Receptacle*.—Diameter: approximately 1.0 cm on average. — depth: approximately 1.0 cm on average. — shape: urn shaped. — color: Yellow-Green Group 144A with some Red-Purple Group 59A. — surface texture: smooth.

*Pollen*.—Amount: sparse. — color: Yellow-Orange Group 20A.

*Hips/seed*.—None observed.

Development:

*Vegetation*.—Glossy, dark green, vigorous.

*Blossoming*.—Abundant and continuous from spring through frost; typically, in bloom outdoors from May to November in Southeastern Pennsylvania.

*Resistance to diseases*.—Excellent resistance for powdery mildew (*Podosphaera pannosa*) and leaf spot (*Cercospora rosicola*).

*Hardiness*.—Hardy to USDA Zone 6; further hardiness testing is in progress.

The new 'KORneukap' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of floribunda rose plant named 'KORneukap' characterized by the following combination of characteristics:

(a) forming orange-colored blossoms, (b) exhibiting a very bushy and upright growth habit, and (c) providing ornamental glossy, dark green foliage;

substantially as herein shown and described.

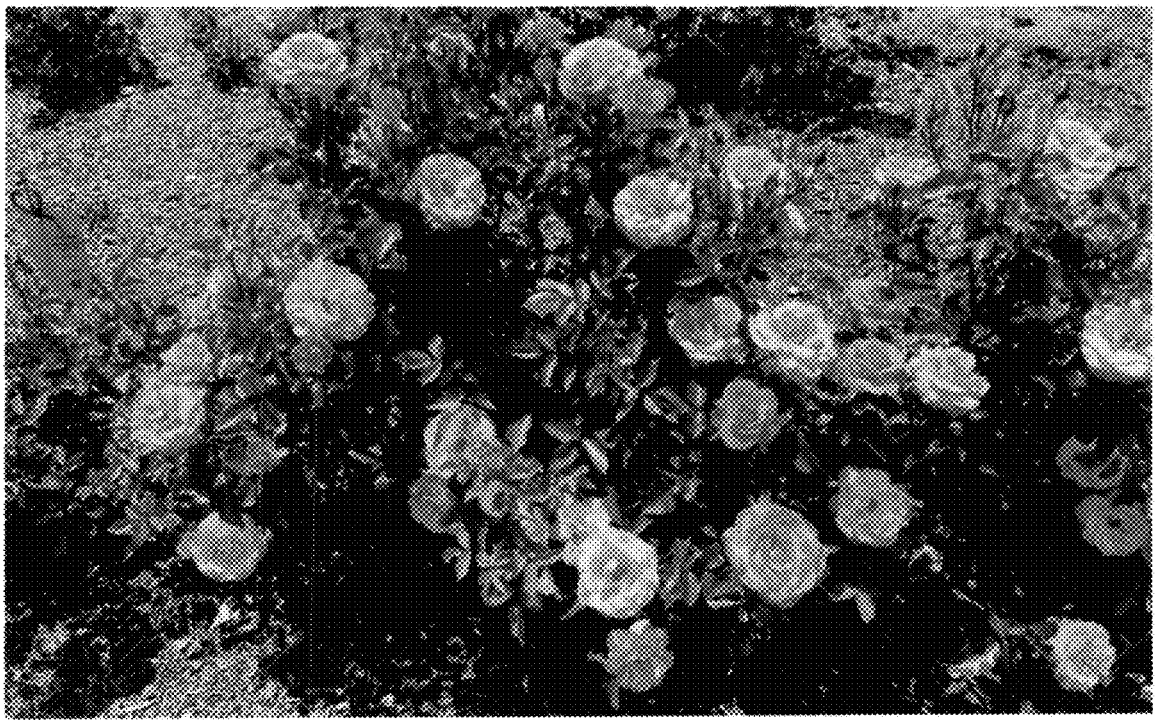

* * * * *